United States Patent
Slemmen et al.

(10) Patent No.: US 9,694,141 B2
(45) Date of Patent: Jul. 4, 2017

(54) NEEDLE SAFETY DEVICE

(71) Applicant: Sanofi-Aventis Deutschland GmbH, Frankfurt am Main (DE)

(72) Inventors: John Slemmen, Merseyside (GB); Chris Ward, Prestatyn (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 478 days.

(21) Appl. No.: 14/349,471

(22) PCT Filed: Oct. 4, 2012

(86) PCT No.: PCT/EP2012/069627
§ 371 (c)(1),
(2) Date: Apr. 3, 2014

(87) PCT Pub. No.: WO2013/050475
PCT Pub. Date: Apr. 11, 2013

(65) Prior Publication Data
US 2014/0249481 A1  Sep. 4, 2014

(30) Foreign Application Priority Data

Oct. 6, 2011  (EP) .................................... 11184100

(51) Int. Cl.
*A61M 5/32* (2006.01)
(52) U.S. Cl.
CPC .......... *A61M 5/3245* (2013.01); *A61M 5/326* (2013.01); *A61M 5/3271* (2013.01);
(Continued)

(58) Field of Classification Search
CPC ................ A61M 5/3245; A61M 5/326; A61M 2005/3267; A61M 2005/3247; A61M 5/3271
See application file for complete search history.

(56) References Cited

U.S. PATENT DOCUMENTS

| 4,681,567 A | 7/1987 | Masters et al. |
| 5,104,385 A | 4/1992 | Huband |
| (Continued) | | |

FOREIGN PATENT DOCUMENTS

| JP | 2008-528225 | 7/2008 |
| WO | 9220390 A1 | 11/1992 |
| WO | 2006081460 A2 | 8/2006 |

OTHER PUBLICATIONS

International Search Report and Written Opinion in International Application No. PCT/EP2012/069627, mailed Jun. 6, 2013, 9 pages.
(Continued)

*Primary Examiner* — Nathan R Price
*Assistant Examiner* — Melissa A Snyder
(74) *Attorney, Agent, or Firm* — Fish & Richardson P.C.

(57) ABSTRACT

Described is a needle safety device comprising a needle hub including a plurality of resilient arms having detents, a needle having a distal tip, and a needle shield telescopically coupled to the needle hub. The needle shield includes a plurality of axial slots adapted to engage the detents on the resilient arms and the detents are axially movable in the slots. The needle shield includes a plurality of grooves separated from the slots by separation walls and the grooves are adapted to engage the detents. When the needle shield is in a first position relative to the needle hub, the needle shield covers the distal tip of the needle and the detents are engaged in the slots. When the needle shield is in a second position relative to the needle hub, the distal tip of the needle protrudes through an aperture in the needle shield and the detents are engaged in the slots. When the needle shield is in a third position relative to the needle hub, the needle shield covers the distal tip of the needle and the detents are engaged in the grooves. In the third position, the detents are (Continued)

adapted to abut the separation walls and prevent proximal movement of the needle shield relative to the needle hub.

11 Claims, 7 Drawing Sheets

(52) U.S. Cl.
 CPC ............... *A61M 2005/3247* (2013.01); *A61M 2005/3267* (2013.01)

(56) References Cited

U.S. PATENT DOCUMENTS

| | | |
|---|---|---|
| 5,137,521 A | 8/1992 | Wilkins |
| 5,919,165 A * | 7/1999 | Benson ............... A61M 5/3216 604/110 |
| 2005/0228345 A1 | 10/2005 | Yang et al. |
| 2007/0060897 A1 | 3/2007 | Wang |
| 2007/0232998 A1 | 10/2007 | Yang et al. |
| 2008/0200881 A1 | 8/2008 | Emmott et al. |
| 2011/0118667 A1* | 5/2011 | Zaiken ............... A61M 5/3202 604/138 |
| 2011/0160675 A1* | 6/2011 | Ruan ................... A61M 5/3272 604/198 |

OTHER PUBLICATIONS

International Preliminary Report on Patentability in International Application No. PCT/EP2012/069627, dated Apr. 8, 2014, 6 pages.
Rote Liste, "50. Hypophysen-, Hypothalamushormone, andere regulatorische Peptide u. ihre Hemmstoffe," Chapter 50, ed. 2008, 20 pages.

* cited by examiner

NEEDLE SAFETY DEVICE

CROSS REFERENCE TO RELATED APPLICATIONS

The present application is a U.S. National Phase Application pursuant to 35 U.S.C. §371 of International Application No. PCT/EP2012/069627 filed Oct. 4, 2012, which claims priority to European Patent Application No. 11184100.3 filed Oct. 6, 2011. The entire disclosure contents of these applications are herewith incorporated by reference into the present application.

FIELD OF INVENTION

It is an object of the present invention to provide an improved safety needle assembly that minimizes the risk of an accidental needle stick injury, that is safe to handle, and that provides needle safety before and after the medicament is delivered.

BACKGROUND

Medicament delivery devices (e.g., pen injectors, syringes, auto-injectors, etc.) that contain a selected dosage of a medicament are well known devices for administering the medicament to a patient. Safety devices for covering a needle of the delivery device before and after use are also well known. Typically, a needle shield of the safety device is either manually moved or automatically to surround the medical needle. Various attempts have been made to develop an optimally sized and functioning safety device. However, there remains a need for an optimal safety needle assembly.

SUMMARY

In an exemplary embodiment, a needle safety device comprises a needle hub including a plurality of resilient arms having detents, a needle having a distal tip, and a needle shield telescopically coupled to the needle hub. The needle shield includes a plurality of axial slots adapted to engage the detents on the resilient arms and the detents are axially movable in the slots. The needle shield includes a plurality of grooves separated from the slots by separation walls and the grooves are adapted to engage the detents. When the needle shield is in a first position relative to the needle hub, the needle shield covers the distal tip of the needle and the detents are engaged in the slots. When the needle shield is in a second position relative to the needle hub, the distal tip of the needle protrudes through an aperture in the needle shield and the detents are engaged in the slots. When the needle shield is in a third position relative to the needle hub, the needle shield covers the distal tip of the needle and the detents are engaged in the grooves. In the third position, the detents are adapted to abut the separation walls and prevent proximal movement of the needle shield relative to the needle hub.

In an exemplary embodiment, the needle hub includes recesses adapted to receive the detents when the arms deflect. The detents include proximal ramped surfaces, and the separation walls have distal ramped surfaces adapted to engage the proximal ramped surfaces of the detents. Engagement of the distal ramped surfaces of the separation walls and the proximal ramped surfaces of the detents causes the arms to deflect radially.

In an exemplary embodiment, the separation walls have proximal abutment surfaces adapted to abut the detents in the third position.

In an exemplary embodiment, the needle safety device further comprises a spring biasing the needle shield relative to the needle hub toward the first and third positions.

In an exemplary embodiment, the needle safety device further comprises a collar coupled to the needle hub by breakable webs. The needle shield includes a proximal end portion adapted to engage the webs. When the needle shield is moving from the first position to the second position, the proximal end portion breaks the webs. The proximal end portion includes a latch to engage the collar.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only and thus are not limitive of the present invention, and wherein.

Corresponding parts are marked with the same reference symbols in all figures.

DETAILED DESCRIPTION

FIGS. 1 to 4B show an exemplary embodiment of a needle safety device 1 according to the present invention. In an exemplary embodiment, the needle safety device 1 includes a needle hub 3, a needle 2 coupled to the needle hub 3, a needle shield 4 telescopically coupled to the needle hub 3 and a compression spring 5 applying a biasing force to the needle hub 3. The needle safety device 1 may be removably coupled to a medicament delivery device (e.g., a syringe, a pen injector, an auto-injector, etc.) or be formed integrally with the delivery device.

The needle safety device 1 serves to reduce the risk of an accidental needlestick injury by covering a distal tip 2.1 of the needle 2 before and after injection of a medicament.

Figure 1:
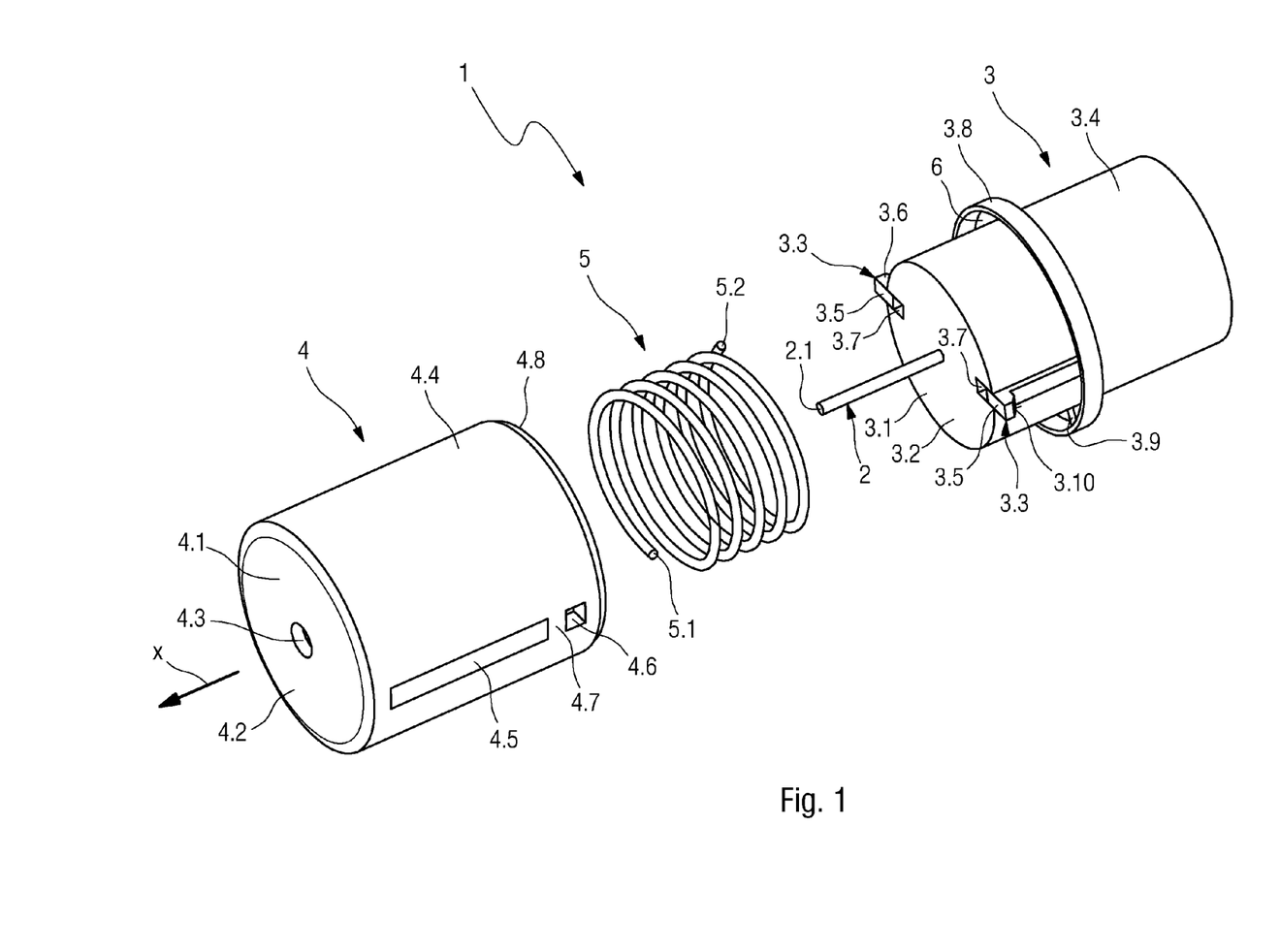
FIG. 1 shows a perspective exploded view of an exemplary embodiment of a needle safety device comprising a main body, a needle shield and a compression spring.
Figure 2:
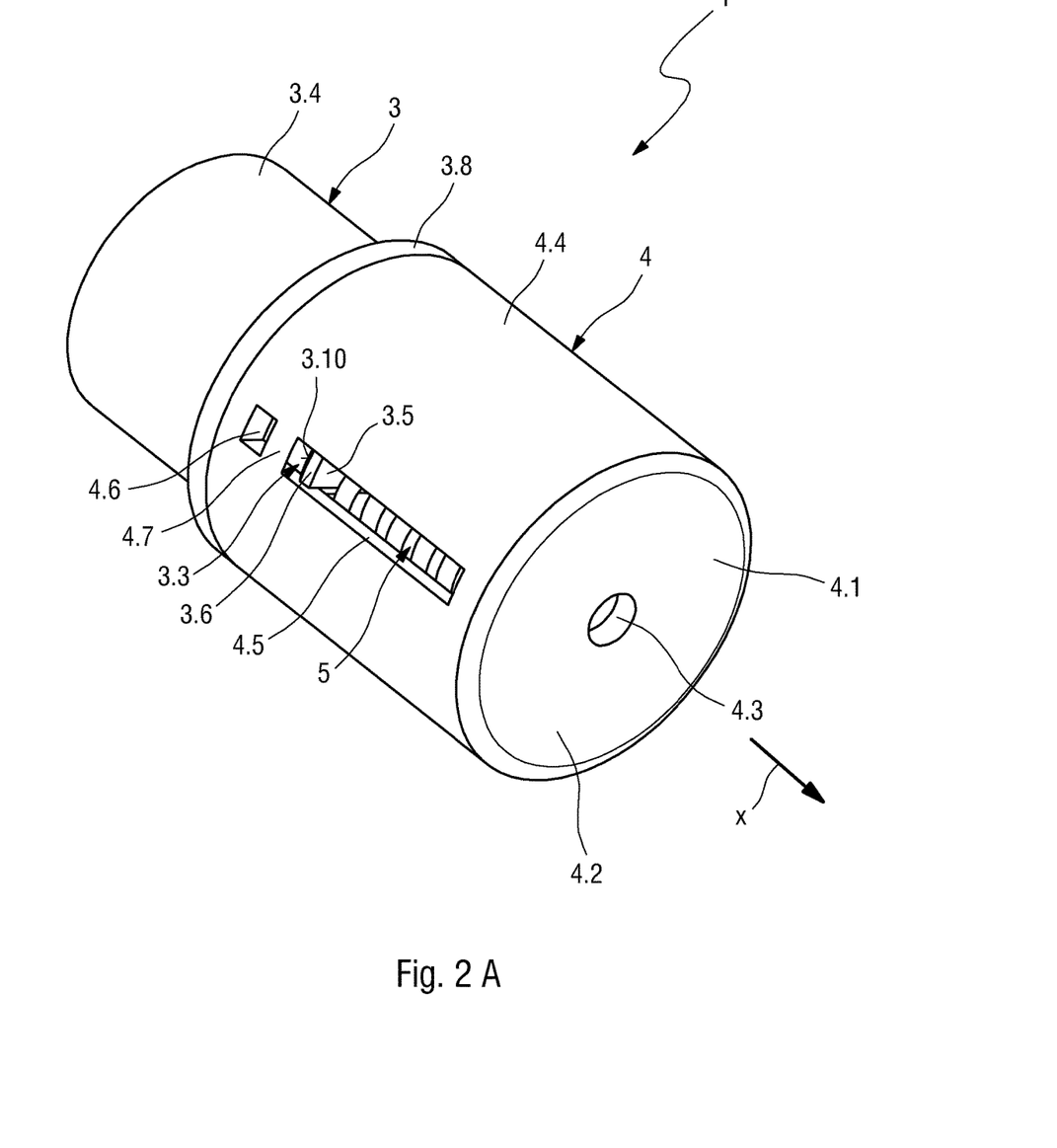
FIG. 2A shows a perspective view of an exemplary embodiment of a needle safety device in an initial position.
FIG. 2B shows a perspective view of an exemplary embodiment of a needle safety device in an initial position.

FIG. 1 shows a perspective exploded view of an exemplary embodiment of a needle safety device 1 according to the present invention. The safety device 1 includes a needle hub 3 adapted to be coupled to the delivery device. For example, the needle hub 3 may include threads, a snap-fit, a bayonet fit, a frictional fit, etc. to couple to the delivery device. In another exemplary embodiment, the needle hub 3 may be integrally formed with the delivery device. The needle hub 3 may be shaped substantially as hollow cylinder or any other shape to be adapted to couple to the delivery device.

The needle 2 may be coupled to the needle hub 3 such that a distal tip 2.1 extends distally beyond a distal face 3.1 of the needle hub 3. A proximal tip of the needle 2 may extend proximally of the distal face 3.1 and be adapted to pierce a septum of a container of medicament in the delivery device.

In an exemplary embodiment, the needle hub 3 includes two resilient arms 3.3 integrated in a side wall 3.4 of the needle hub 3. Distal ends 3.5 of the resilient arms 3.3 are capable of deflecting radially relative to the needle hub 3. Each distal end 3.5 includes a detent 3.6 which beyond a circumference of the side wall 3.4 of the needle hub 3. The distal face 3.1 of the needle hub 3 includes two recesses 3.7 (e.g., formed in a periphery 3.2 of the distal face 3.1) located adjacent the distal ends 3.5 of the arms 3.3 which are adapted to receive the distal ends 3.5 of the arms 3.3 when the arms 3.3 are deflected radially. When the arms 3.3 arms are deflected radially toward a longitudinal axis x of the needle hub 3, the detents 3.6 may lie in substantially the same plane as the side wall 3.4.

In an exemplary embodiment, the needle hub 3 comprises a collar 3.8 coupled to the needle hub 3. The collar 3.8 may be an annular element or part of an annular element. The collar 3.8 may be coupled to side wall 3.4 of the needle hub 3 by one or more connecting webs 3.9. The webs 3.9 may define predetermined breaking points for breaking the collar 3.8 away from the needle hub 3.

In an exemplary embodiment, the needle shield 4 is telescopically coupled to the needle hub 3. A distal wall 4.2 of the needle shield 4 includes an aperture 4.3 for allowing the needle 2 to pass through (e.g., during an injection). A side wall 4.4 of the needle shield 4 may have axial slots 4.5 which are adapted to engage the arms 3.3 of the needle hub 3. Each slot 4.5 may engage a respective detent 3.6 on the arm 3.3, and the detent 3.6 may be axially movable within the slot 4.5 when the needle shield 4 moves relative to the needle hub 3. Engagement of the detents 3.6 and the slots 4.5 may prevent rotation of the needle shield 4 relative to the needle hub 3. Each of the slots 4.5 is accompanied by a groove 4.6 in the needle shield 4 placed proximal of the respective slot 4.5 and designed to receive the detent 3.6. Each slot 4.5 and the corresponding groove 4.6 may be separated by a separation wall 4.7.

In an exemplary embodiment, a proximal end portion 4.8 of the needle shield 4 may be adapted to fit into a space 6 between the collar 3.8 and the side wall 3.4.

In an exemplary embodiment, the compression spring 5 is grounded distally in the distal end 4.2 of the needle shield 4 and proximally in the distal face 3.1 of the needle hub 3.

FIGS. 2A and 2B show the needle safety device 1 in an initial state (e.g., prior to use) in which the needle shield 4 is in a first, extended position relative to the needle hub 3. In the first position, the distal tip 2.1 of the needle 2 is fully covered by the needle shield 4. The detents 3.6 on the arms 3.3 are engage in the slots 4.5 and located at proximal ends of the slots 4.5. In an exemplary embodiment, the compression spring 5 may be pre-stressed, pressing the proximal end of the needle shield 4 against the collar 3.8 with a force not sufficient to break the connecting webs 3.9. Because the spring 5 is pre-stressed, the detents 3.6 may abut the separation wall 4.7, which prevents the needle shield 4 from moving distally relative to the needle hub 3.

As shown in the exemplary embodiment in FIG. 2B, the detents 3.6 may include proximal ramped surfaces 3.10, and the separation walls 4.7 may include distal ramped surfaces 4.9 adapted to engage the proximal ramped surfaces 3.10 of the detents 3.6. Further, the proximal end portion 4.8 of the needle shield 4 may include a latch adapted to engage the collar 3.8.

Figure 3:
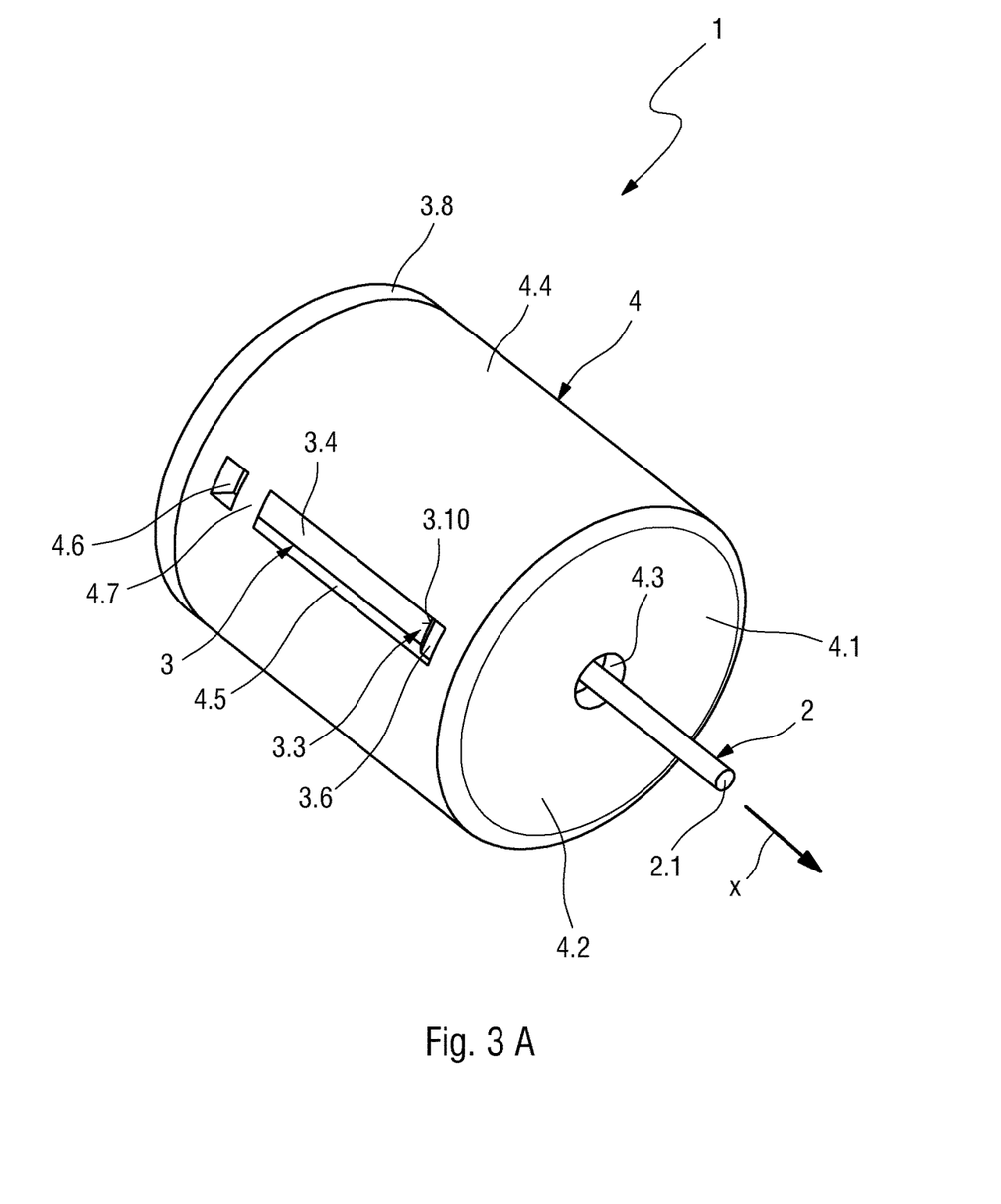
FIG. 3A shows a perspective view of an exemplary embodiment of a needle safety device in a delivery position.
FIG. 3B shows a perspective view of an exemplary embodiment of a needle safety device in a delivery position.
Figure 3B:
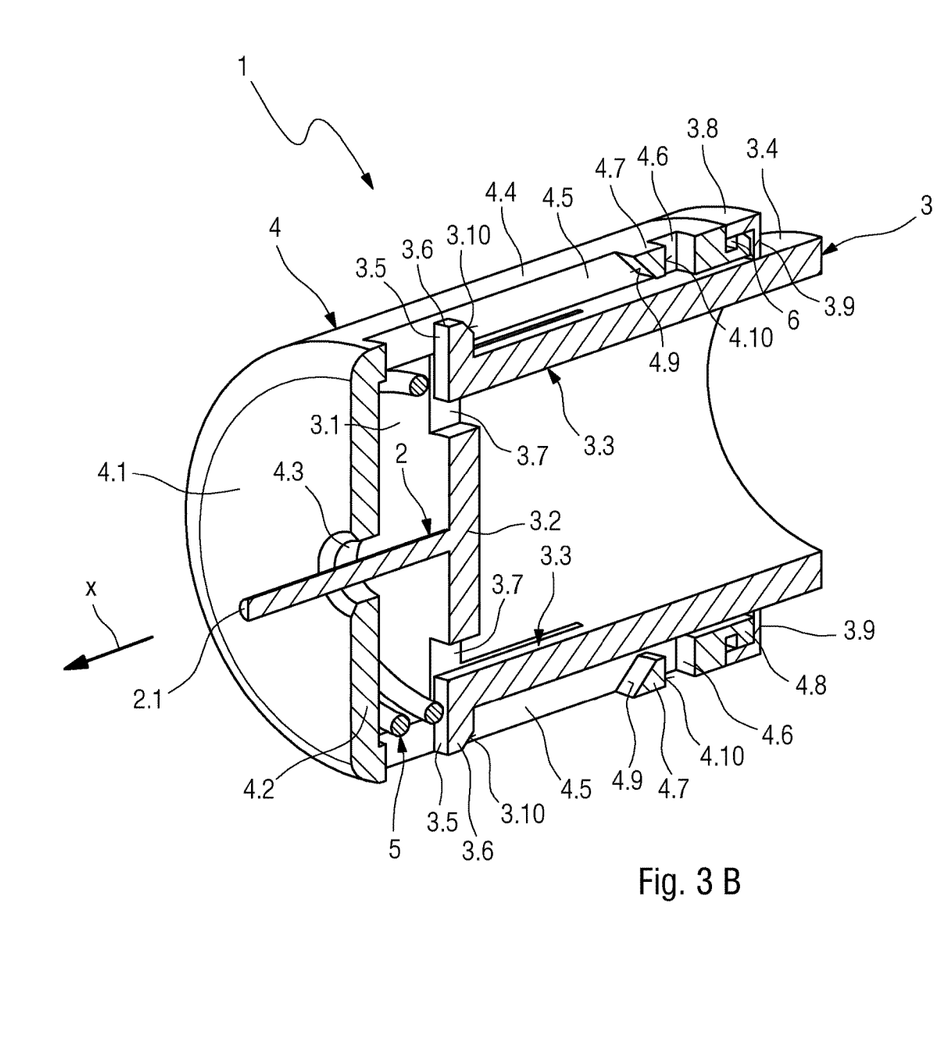
Figure 4:
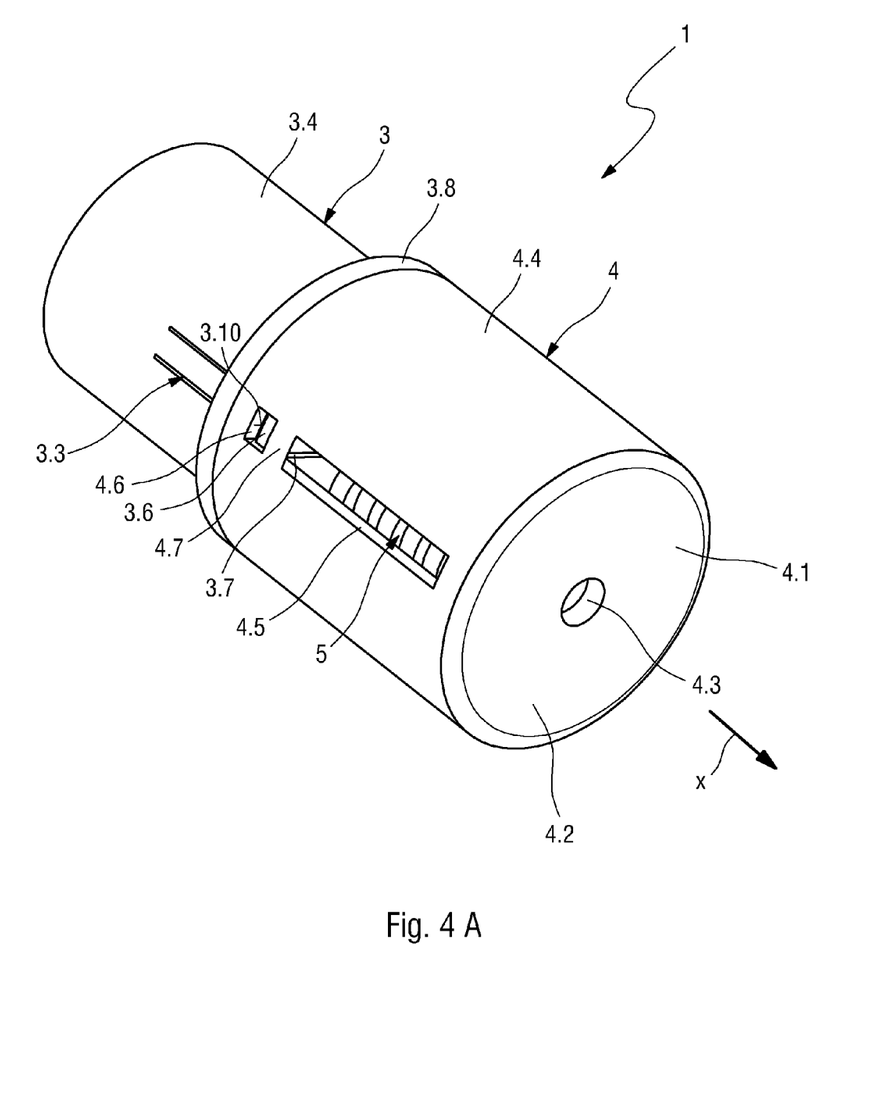
FIG. 4A shows a perspective view of an exemplary embodiment of a needle safety device in a locked position.
FIG. 4B shows a perspective view of an exemplary embodiment of a needle safety device in a locked position.

FIGS. 3A and 3B show the needle safety device 1 in an intermediate state (e.g., during an injection when the needle safety device 1 is pressed against an injection site) in which the needle shield 4 is in a second, refracted position relative to the needle hub 3. When proximally-directed force is applied to the needle shield 4, the needle shield 4 moves proximally relative to the needle hub 3 causing the proximal end portion 4.8 of the needle shield 3 to break the webs 3.9, separating the collar 3.8 from the needle hub 3. When the needle shield 4 has reached the second position, the distal tip 2.1 of the needle protrudes through the distal aperture 4.3 of the needle shield 4. Further, in the second position, the detents 3.6 have moved distally within the slots 4.5 until they are stopped by the compression spring 5 and/or the distal end of the slots 4.5.

FIGS. 4A and 4B show the needle safety device 1 in a final state (e.g., after an injection and the needle safety device 1 has been removed from the injection site) in which the needle shield 4 is in a third, extended position relative to the needle hub 3. When the needle safety device 1 is removed from the injection site, the spring 5 forces the needle shield 4 to move distally relative to the needle hub until each detent 3.6 hits the separation wall 4.7. When the detent 3.6 engages the separation wall 4.7, the proximal ramped surface 3.10 of the detent 3.6 engages distal ramped surface of the separation 4.7 which causes the arm 3.3 to deflect radially toward the axis x. When the detent 3.6 has bypassed the separation wall 4.7, the arm 3.3 returns to its undeflected position and the detent 3.6 is secured in the groove 4.6.

In third position, the needle safety device 1 is needle-safe, because the needle shield 4 covers the distal tip 2.1 of the needle 2. And, the needle shield 4 is prevented from moving proximally relative to the needle hub 3, because the detent 3.6 abuts a proximal abutment face of the separation wall 4.7.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle safety device comprising:
   a needle hub including a plurality of resilient arms having detents;
   a needle having a distal tip;
   a needle shield telescopically coupled to the needle hub, the needle shield including a plurality of axial slots adapted to engage the detents on the resilient arms and wherein the detents are axially movable in the slots and adapted to engage the slots so as to inhibit rotation of the needle shield relative to the needle hub, the needle shield including a plurality of grooves separated from the slots by separation walls and wherein the grooves are adapted to engage the detents; and
   a spring positioned between the needle hub and the needle shield;

wherein, when the needle shield is in a first position relative to the needle hub, the needle shield covers the distal tip of the needle and the detents are positioned in proximal ends of the slots and are adapted to abut the separation walls to inhibit distal movement of the needle shield relative to the needle hub, wherein, when the needle shield is in a second position relative to the needle hub, the distal tip of the needle protrudes through an aperture in the needle shield and the detents are positioned in distal ends of the slots, and wherein, when the needle shield is in a third position relative to the needle hub, the needle shield covers the distal tip of the needle and the detents are engaged in the grooves, wherein the spring is configured to, when the needle shield is in the second position and is removed from an injection site, bias the needle shield into the third position such that the detents move through the proximal ends of the slots and bypass the separation walls, and wherein, in the third position, the detents are adapted to abut the separation walls to inhibit proximal movement of the needle shield relative to the needle hub.

2. The needle safety device according to claim 1, wherein the needle hub includes recesses adapted to receive the detents when the arms deflect.

3. The needle safety device according to claim 1, wherein the detents include proximal ramped surfaces.

4. The needle safety device according to claim 3, wherein the separation walls have distal ramped surfaces adapted to engage the proximal ramped surfaces of the detents.

5. The needle safety device according to claim 4, wherein engagement of the distal ramped surfaces of the separation walls and the proximal ramped surfaces of the detents causes the arms to deflect radially.

6. The needle safety device according to claim 1, wherein the separation walls have proximal abutment surfaces adapted to abut the detents in the third position.

7. The needle safety device according to claim 1, further comprising a collar coupled to the needle hub by breakable webs.

8. The needle safety device according to claim 7, wherein the needle shield includes a proximal end portion adapted to engage the webs.

9. The needle safety device according to claim 8, wherein, when the needle shield is moving from the first position to the second position, the proximal end portion breaks the webs.

10. The needle safety device according to claim 7, wherein the webs are configured such that a spring force of the spring on the needle shield is insufficient to break the webs.

11. The needle safety device according to claim 7, wherein a proximal portion of the needle shield is configured to break the webs when the needle shield moves proximally relative to the needle hub from the first position toward the second position.

* * * * *